(12) United States Patent
Paranjpe et al.

(10) Patent No.: US 10,835,301 B1
(45) Date of Patent: Nov. 17, 2020

(54) MALLEABLE AUXILIARY COMPRESSION PLATE SYSTEM AND METHOD

(71) Applicant: Curax Scientific, LLC, St. Louis, MO (US)

(72) Inventors: Amod P. Paranjpe, Augusta, MO (US); A. Jamie Riley, St. Louis, MO (US); Gary J. Schmidt, St. Louis, MO (US)

(*) Notice: Subject to any disclaimer, the term of this patent is extended or adjusted under 35 U.S.C. 154(b) by 647 days.

(21) Appl. No.: 14/657,718

(22) Filed: Mar. 13, 2015

Related U.S. Application Data (60) Provisional application No. 61/952,845, filed on Mar. 13, 2014.

(51) Int. Cl.
*A61B 17/80* (2006.01)
*A61B 17/68* (2006.01)

(52) U.S. Cl.
CPC ...... *A61B 17/8004* (2013.01); *A61B 17/8009* (2013.01); *A61B 2017/681* (2013.01)

(58) Field of Classification Search
CPC . A61B 17/80; A61B 17/8004; A61B 17/8009; A61B 17/8014; A61B 17/8085; A61B 2017/681; A61B 17/8066; A61B 17/8071; A61B 17/8076; A61B 17/8061
See application file for complete search history.

(56) References Cited

U.S. PATENT DOCUMENTS

| | | | | |
|---|---|---|---|---|
| 1,156,440 A | * | 10/1915 | Smith | A61B 17/80 606/70 |
| 5,718,705 A | * | 2/1998 | Sammarco | A61B 17/8085 606/260 |
| 6,093,188 A | | 7/2000 | Murray | |
| 7,635,365 B2 | | 12/2009 | Ellis et al. | |
| 8,226,693 B2 | | 7/2012 | Reimels et al. | |
| 9,808,297 B2 | * | 11/2017 | Bernstein | A61B 17/80 |
| 2006/0085000 A1 | * | 4/2006 | Mohr | A61B 17/8076 606/281 |
| 2008/0015590 A1 | * | 1/2008 | Sanders | A61B 17/80 606/86 A |
| 2012/0226321 A1 | * | 9/2012 | Gonzalez-Hernandez | A61B 17/8061 606/286 |
| 2012/0303068 A1 | * | 11/2012 | Fritzinger | A61B 17/808 606/286 |
| 2013/0053899 A1 | * | 2/2013 | Bluechel | A61B 17/8061 606/281 |

(Continued)

FOREIGN PATENT DOCUMENTS

| | | | | |
|---|---|---|---|---|
| JP | 03012145 A | * | 1/1991 | ......... A61B 17/8085 |
| WO | 9007304 A1 | | 7/1990 | |
| WO | WO9418910 A1 | * | 9/1994 | |

*Primary Examiner* — Christie L Bahena
(74) *Attorney, Agent, or Firm* — Sandberg Phoenix & von Gontard, P.C.

(57) ABSTRACT

A compression plate for use with treating a fracture on a bone includes a main body portion comprising a pair of opposing ends and a pair of arms. Each arm of the pair of arms extending from a respective end of the pair of opposing ends. The compression plate also includes a bending feature defined in at least one of the main body portion and the arms. The bending feature is configured to enable deflection of at least one of the main body portion and the arms such that the bending feature applies a compression force on the bone.

14 Claims, 7 Drawing Sheets

(56) References Cited

U.S. PATENT DOCUMENTS

2013/0178905 A1* 7/2013 Graham ............... A61B 17/808
 606/282
2015/0209093 A1* 7/2015 Dallis ................ A61B 17/8023
 606/281

* cited by examiner

MALLEABLE AUXILIARY COMPRESSION PLATE SYSTEM AND METHOD

CROSS REFERENCE TO RELATED APPLICATIONS

This application claims priority to U.S. Provisional Application No. 61/952,845 filed on Mar. 13, 2014, which is hereby incorporated by reference in its entirety.

BACKGROUND

The present disclosure relates generally to systems and methods of applying compression when neutralizing a bone fracture, and, more specifically, to systems and methods of utilizing a compression plate to apply compression during an orthopedic procedure.

Orthopedic procedures often demand the application of significant forces in specific ways and/or directions, or combinations thereof. Additionally, due to the different ways in which a fracture or other bone malady may present itself, there can be a need to access and/or apply force to a multitude of sights in single procedure. The details of the injury and anatomy being treated dictate how the procedure is performed and generally do not tailor themselves to the skill of the surgeon or the ease of use of the available equipment.

One major factor that contributes to a surgeon's challenges is limitations on access to the "work site". Visual access to the work site may be limited due to fluids and tissues present within the patient and the associated equipment required to handle such tissues and fluids. Available space to execute the orthoscopic actions at the work site can be even more obstructed, for example by the equipment described above, than the visual access. In the process of reducing and eventually neutralizing a fracture, it is frequently desirable to apply an appropriate compressive force across a fracture site to promote healing. Currently, at least one known system applies the required force with a clamp that extends above and around the cortical plate used to bridge the fracture. As such, the clamp impedes both visual and physical closing of the site such that the desirable compressive force provided by the clamp is not maintained during healing.

BRIEF DESCRIPTION

In one aspect, a compression plate for use with treating a fracture on a bone is provided. The compression plate includes a main body portion comprising a pair of opposing ends and an arm extending from each end of the pair of opposing ends. The compression plate also includes a bending feature defined in at least one of the main body portion and the arms. The bending feature is configured to enable deflection of at least one of the main body portion and the arms such that the bending feature applies a compression force on the bone.

In another aspect, a compression plate assembly for use with treating a fracture on a bone is provided. The compression plate assembly includes a cortical plate and a compression plate coupled to the cortical plate such that the compression plate is positioned between the bone and the cortical plate. The compression plate includes a main body portion comprising a pair of opposing ends and an arm extending from each end of the pair of opposing ends. The compression plate also includes a bending feature defined in at least one of the main body portion and the arms. The bending feature is configured to enable deflection of at least one of the main body portion and the arms such that the bending feature applies a compression force on the bone.

DETAILED DESCRIPTION

Figure 1:
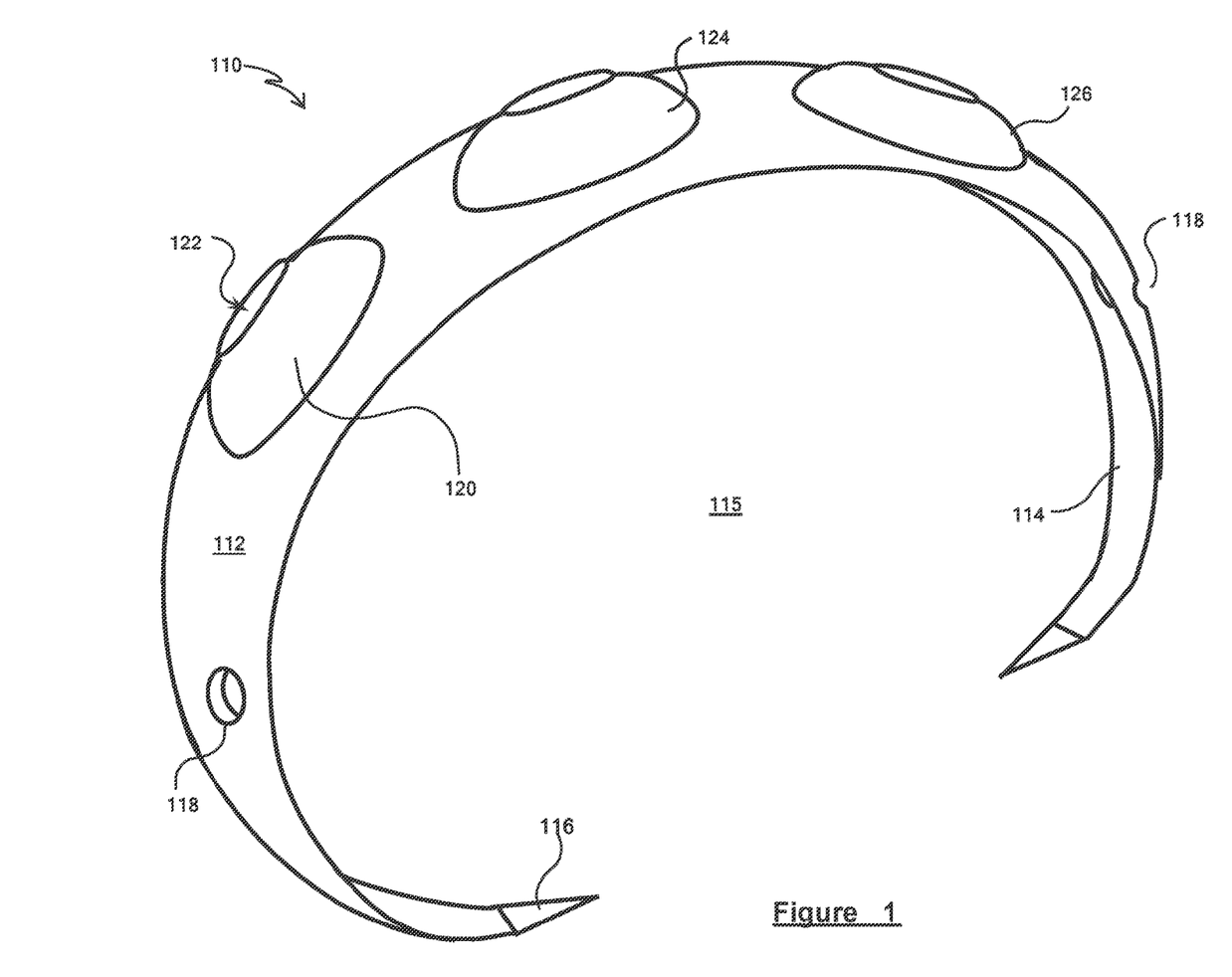
FIG. 1 is a perspective view of an exemplary compression plate.

FIG. 1 illustrates a perspective view of an exemplary malleable compression plate 110. In the exemplary embodiment, plate 110 is substantially C-shaped and is configured to fit around a patient's bone during an orthoscopic procedure. More specifically, plate 110 extends over a fracture in the patient's bone and applies a compression force to different parts of the bone to maintain the bone in the proper position. Plate 110 includes a main body portion 112 and a pair of arms 114 extending outward from opposing ends of main body portion 112. Arms 114 and main body portion 112 form a C-shaped band that defines a central void 115 that, during use, is occupied by the patient's bone. In the exemplary embodiment, each arm 114 terminates in a distal end 116 that includes a prong configured to maintain contact with the bone. In one embodiment, prongs 116 are formed from a different material than body 112 and arms 114 to provide prongs with an increased grip strength during use.

Alternatively, prongs 116 may be formed from the same material as body 112 and arms 114. Plate 110 further includes at least one k-wire or screw hole 118 defined in at least one of main body portion 112 and arms 114. Additionally, main body portion 112 includes a plurality of screw assemblies 120 for receiving a screw (not shown) to attach plate 110 to the bone. More specifically, each screw assembly 120 includes an aperture 122 defined therethrough to receive the screw and a rounder shoulder 124 that extends outward away from void 115.

Figure 2:
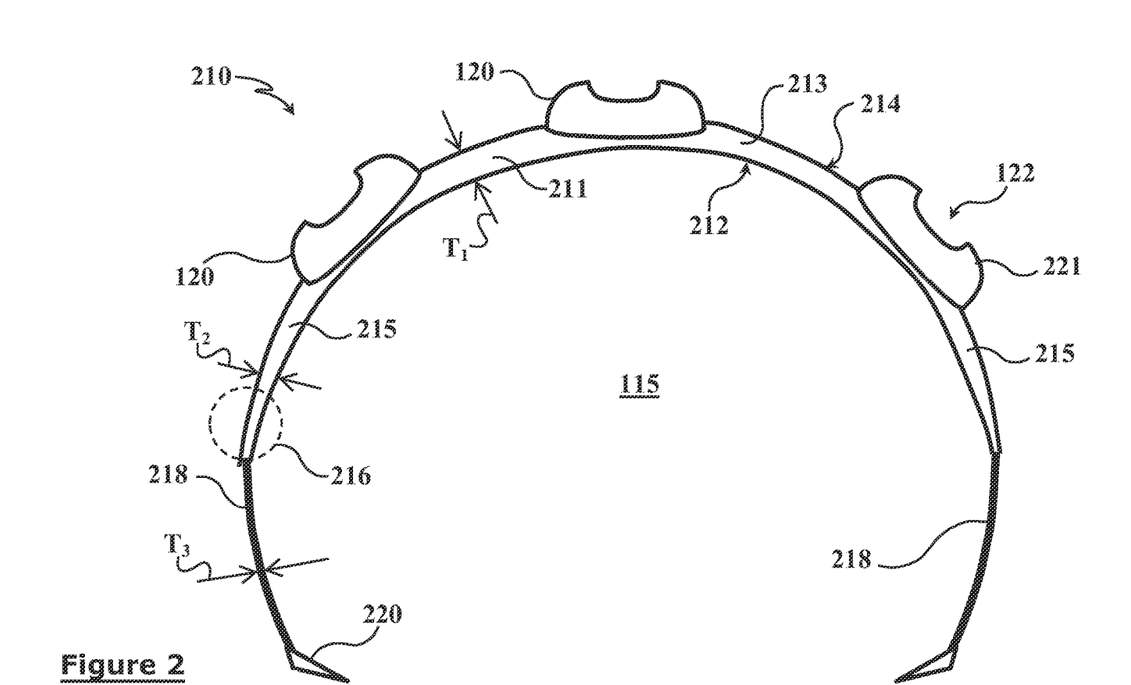
FIG. 2 is a side view of another embodiment of a compression plate.
Figure 3:
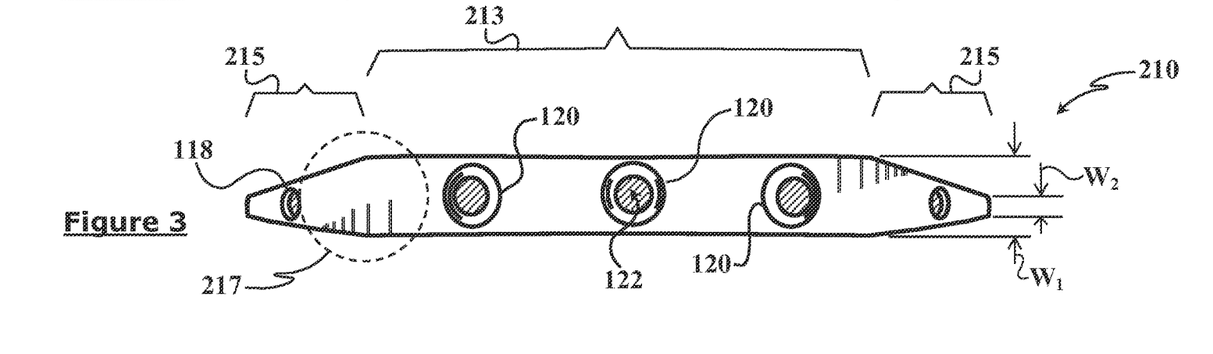
FIG. 3 is a top view of the compression plate shown in FIG. 2.

FIG. 2 is a side view of another embodiment of a malleable compression plate 210, and FIG. 3 is a top view of compression plate 210. As shown in FIGS. 2 and 3, plate 210 also includes screw assemblies 120 and screw holes 118 that are similar to those described above with reference to plate 110 (shown in FIG. 1), although screw assembly 120 includes a shoulder 221 having a different profile than shoulder 124 (shown in FIG. 1). In the exemplary embodiment, plate 210 includes a main body 211 having a bottom inner surface 212 and a top outer surface 214 that define a thickness of main body 211. Main body portion 211 also includes a central body portion 213 and a pair of opposing end body portions 215 extending from central portion 213 at a transition region 217. As shown in FIG. 2, the thickness of main body portion 211 varies between ends 215. Specifically, central body portion 213 includes a thickness T1 that is greater than a thickness T2 of end portions 215.

In the exemplary embodiment, plate 210 also includes a pair of arms 218 extending from end body portions 215 such that a transition area 216 is defined between each end portion 215 and a respective arm 218. Each arm 218 includes a substantially constant thickness T3 that is less than thickness T1 and T2 of central body 213 and end body portions 215, respectively. Such a difference in thickness facilitates bending of arms 218 inward towards void 115 earlier than main body portion 211 when an increasing crimping force is applied to plate 210. Specifically, under an increasing crimping force, the varying thickness of plate 210 cause arms 218 to bend first, followed by end body portions 215, and finally center body portion 213. Alternatively, portions 213 and 215 and arms 218 may have any thickness that facilitate operation of plate 210 as described herein. As shown in FIG. 3, in the exemplary embodiment, central body portion 213 includes a first width W1 and end body portions 215 include a second width W2 that is smaller than first width W1. Furthermore, first width W1 of central body portion 213 is substantially constant while second width W2 of end body portions 215 tapers from first width W1 to second width W2. Alternatively, portions 213 and 215 may have any width that facilitates operation of plate 210 as described herein.

Figure 4:
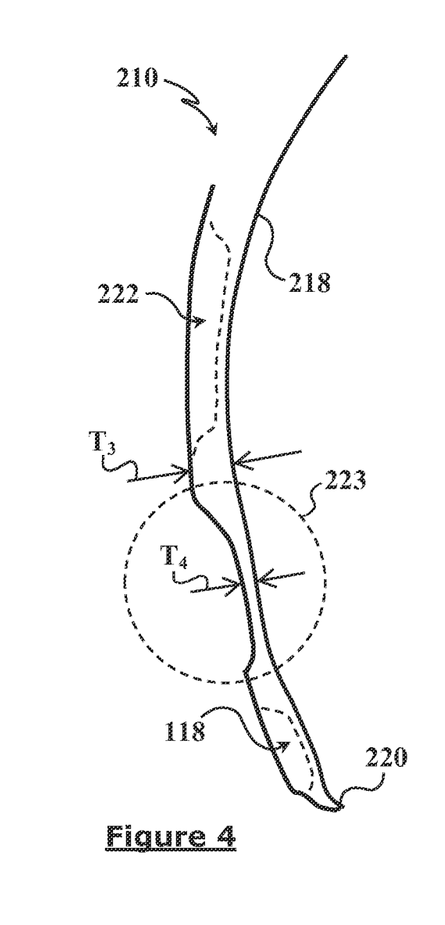
FIG. 4 is a side view of a portion of the compression plate shown in FIG. 2 illustrating a bending feature.

FIG. 4 is a side view of one of arms 218 of plate 210. In the exemplary embodiment, arm 218 also includes a depressed screw hole 222 that is similar to screw assembly 120 (shown in FIG. 2) except that hole 222 extends into plate 210 rather than protruding from it. Furthermore, arm 218 includes a bending feature that facilitates deflecting a portion of arm 218 such that the bending feature applies and/or maintains a compression force on the bone. More specifically, in the exemplary embodiment, the bending feature includes a varying thickness of arm 218 that defines a first arm portion and a second arm portion that is moveable relative to the first arm portion about the bending feature. The bending feature includes a bending segment 223 of arm 218 that includes a fourth thickness T4 that is less than the third thickness T3 of the remainder of arm 218. As described above, the different thicknesses of different portions of arm 218 facilitate moving bending segment 223 under a smaller force than the remainder of arm 218. Although bending segment 223 is described above as a portion of arm 218, bending segment 223 may, alternatively or in combination, be a portion of main body portion 211 (shown in FIG. 2). Additionally, distal end 220 of arm 218 illustrates a hook-shaped prong to facilitate grasping the bone.

Figure 5:
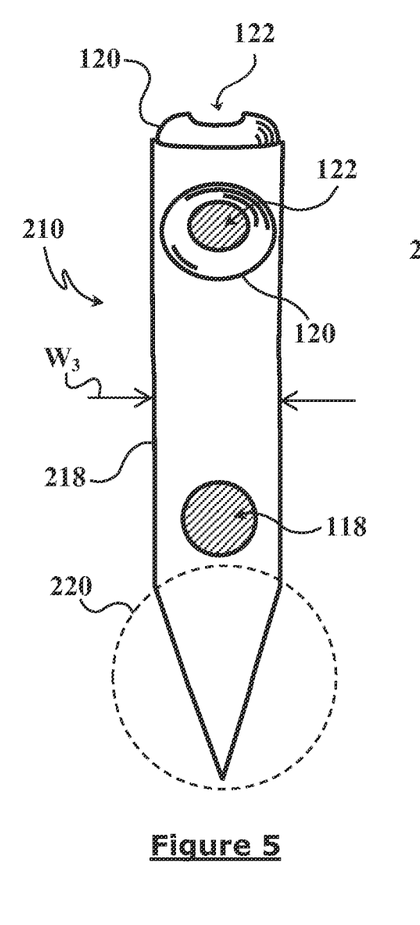
FIG. 5 is an end view the portion of the compression plate shown in FIG. 4.

FIG. 5 is an end view of plate arm 218 illustrating a substantially constant width W3 of arm 218. Alternatively, arms 218 may have a width that decreasingly tapers from transition region 216 (shown in FIG. 2) to distal end 220. Further, distal end 220 of arm may include a tapering point, as shown in FIG. 5, rather than the hook-shaped prong shown in FIG. 4.

Figure 6:
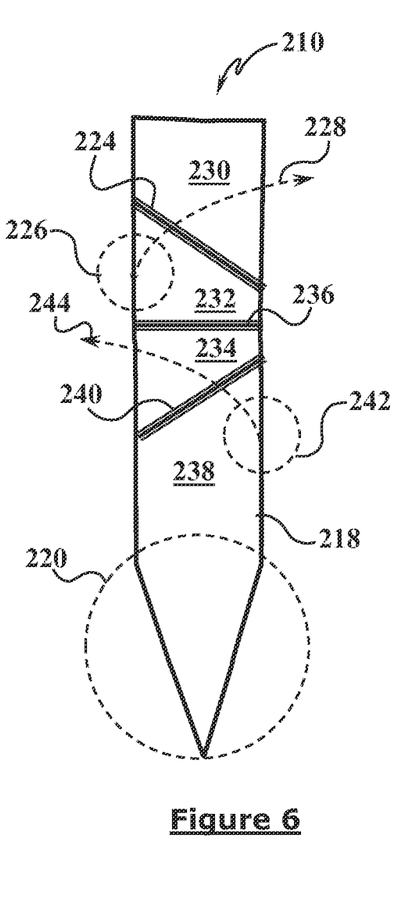
FIG. 6 is an end view the portion of the compression plate shown in FIG. 4 illustrating another bending feature.

FIG. 6 is an end view of arm 218 of plate 210 illustrating another bending feature. In the exemplary embodiment, the bending feature includes a plurality of score marks 224, 236, and 240 located in arm 218. Alternatively, or in combination, score marks 224, 236, and 240 are located on main body portion 211 (shown in FIG. 2) Although three score marks are shown having an illustrated orientation, arms 218 may have any number of score marks having any orientation that facilitates operation of plate 210 as described herein. Generally, a set of score marks, by defining a localized region of bending, will enact specific forms of directed bending between differing portions of arm 218. More specifically, score mark 224, by angling downward from left to right, defines that when a force acts upon arm 218, a first arm portion 226 moves inward toward void 115 (shown in FIG. 2) such that portion 226 pivots about score mark 224 in the general direction of dashed arrow 228. This pivoting about score mark 224 can produce differing degrees of abruptness of change in surface orientation between a first surface 230 on one side of mark 224 and a second surface 232 on an opposite side of mark 224. A deeper score cut will produce a greater degree of abruptness of change in the orientation angle. Similar degrees of abruptness of change in orientation angle between second surface 232 and a third surface 234 can also be controlled by varying the deepness of score cut 236, and the same for third surface 234 and a fourth surface 238, controlled by the depth of a score mark 240. Similar to first arm portion 226 described above, when a force is applied to a second arm portion 242, portion 242 moves inward toward void 115 such that portion 226 pivots about score mark 224 in the general direction of dashed arrow 244. In such a configuration, first portion 226 and second portion 242 are oriented in different directions such that arm 218 bends in three dimensions. In operation, arm 218 may be bent about any combination of score marks 224, 236, and 240 such that score marks 224, 236, and 240 facilitate deflecting at least one portion of arm 218 to apply and/or maintain a compression force on the bone.

Figures 7, 8, 9:
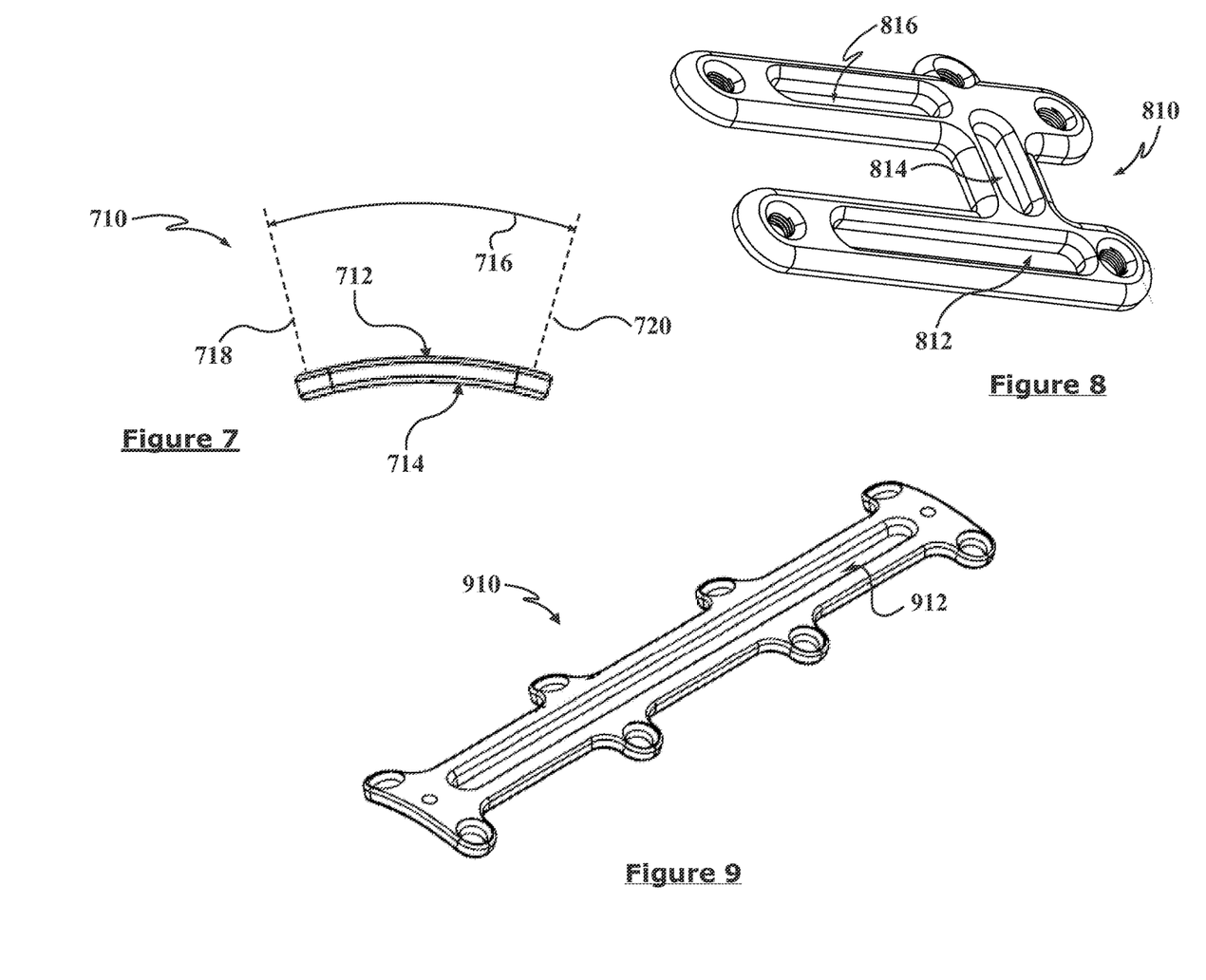
FIG. 7 is an end view of an exemplary cortical plate that may be used with the compression plate shown in FIGS. 1-6.
FIG. 8 is a perspective view of the cortical plate shown in FIG. 7.
FIG. 9 is a perspective view of another embodiment of a cortical plate that may be used with the compression plate shown in FIGS. 1-6.

FIGS. 7-12 illustrate a plurality of cortical plates that may be used with malleable compression plates 110 or 210 described above. However, malleable compression plates 110 and 210 are not limited to use with only those cortical plates shown in FIGS. 7-12. As described in further detail below, many of the plates shown in FIGS. 7-12 are rounded in profile to more closely fit to the bone being repaired. Since the malleable compression plates 110 and 210 described herein are primarily intended to fit between one of these cortical plates and the bone, an even more fitted profile is often required of many embodiments of the malleable compression plates 110 and 210. An illustration of a typical example profile is depicted in FIG. 7, which shows a longitudinal end view of a cortical plate 710 that may be used with malleable compression plates 110 and 210. Cortical plate 710 has upper and lower surfaces, 712 and 714, respectively, that are roughly parallel, and are generally of substantially greater thickness than malleable compression plates 110 and 210. The profile of cortical plate 710 can be measured by determining an angle 716 between normal vectors 718 and 720, for purposes of adapting the design and/or shaped configuration of a particular embodiment of the malleable compression plate.

Figures 10, 11:
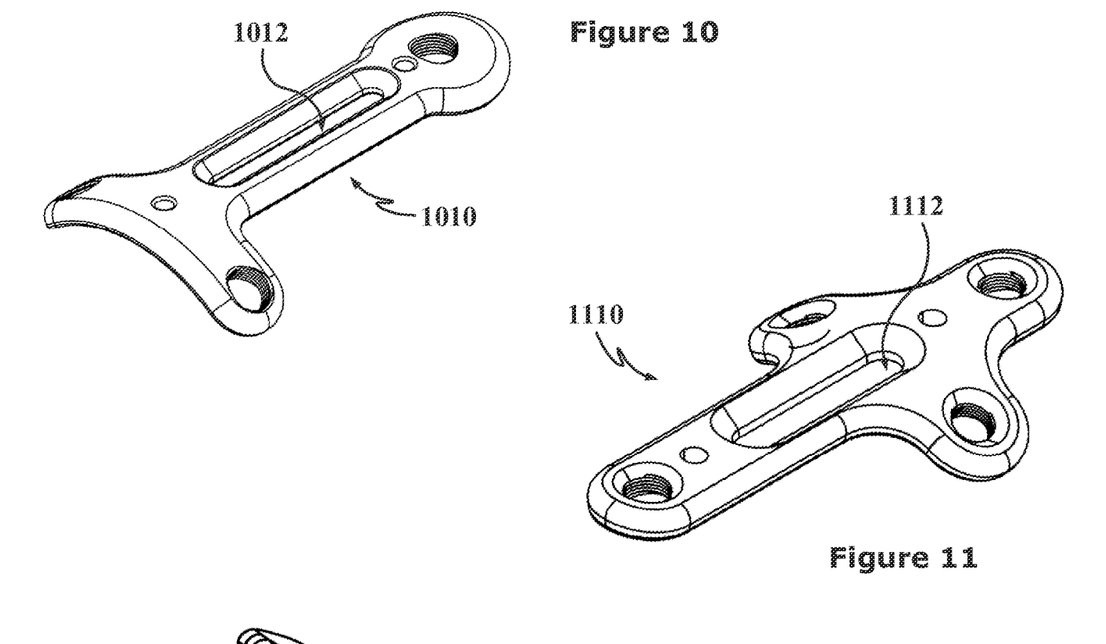
FIG. 10 is a perspective view of yet another embodiment of a cortical plate that may be used with the compression plate shown in FIGS. 1-6.
FIG. 11 is a perspective view of yet another embodiment of a cortical plate that may be used with the compression plate shown in FIGS. 1-6.
Figure 12:
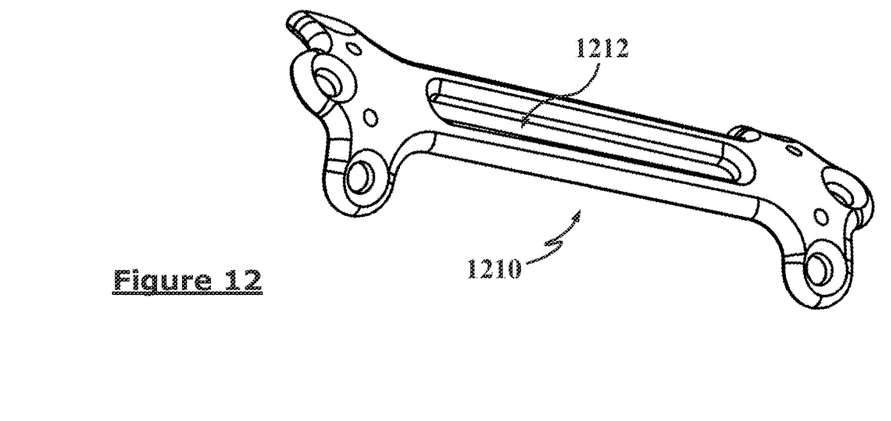
FIG. 12 is a perspective view of yet another embodiment of a cortical plate that may be used with the compression plate shown in FIGS. 1-6.

FIG. 8 illustrates a cortical plate 810 typically utilized for Liz-Franc injuries, that includes first, second, and third, interactive slots 812, 814, and 816 that are suited for cooperative interaction with malleable compression plates 110 and 210, in particular those malleable compression plates 110 and 210 that include elevated areas such as the raised screw assemblies 120 (shown in FIG. 2), as described in further detail below. FIG. 9 depicts an elongated cortical plate 910 that includes an elongated cooperative slot 912. FIG. 10 depicts a short, highly curled; three screw plate 1010 with an extending cooperative slot 1012. FIG. 11 depicts a short, highly curled, four hole plate 1110 with an extending cooperative slot 1112. FIG. 12 depicts a modest, curled, six hole plate 1210 with a moderately extending cooperative slot 1212.

Figures 13, 14:
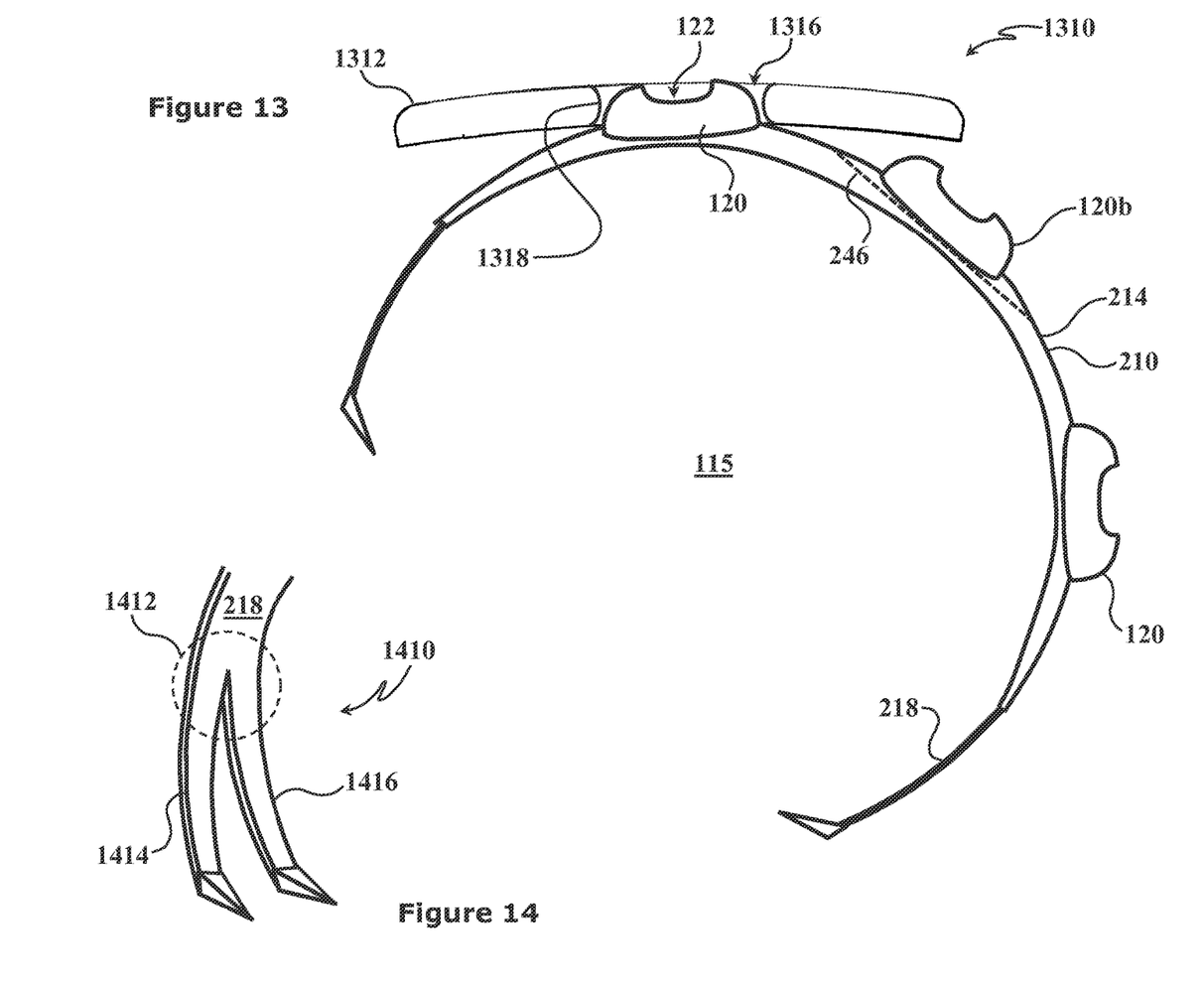
FIG. 13 is a side view of an exemplary compression plate assembly illustrating a compression plate and a cortical plate.
FIG. 14 is a perspective view of a double-arm variant of the compression plate shown in FIG. 2.

FIG. 13 depicts a side view of a compression plate assembly 1310 including a generically representative cortical plate 1312 coupled to malleable compression plate 210. In the exemplary embodiment, cortical plate 1312 is any of plates 810, 910, 1010, 1110, and 1210. Cortical plate 1312 includes an elongated slot 1316, defined by internal slot walls 1318, that is configured to engage a raised screw assembly 120 of compression plate 210. The rounded profile of shoulder 221 (shown in FIG. 2) enables relative rotation of cortical plate 1312 to compression plate 210 once engagement is obtained. Furthermore, because slot 1316 is elongated, cortical plate 1312 can translate back and forth while maintaining the cooperative relationship with compression plate 210. An important resulting benefit of utilizing plate assembly 1310 is that the surgeon can apply a specific selected compression first, and then distract and/or reduce the fracture, and even neutralize the fracture, all while the compression provided by compression plate 210 is continued, and even though the bone being compressed may move during the reduction, distraction, and/or neutralization. As such, compression in a selected direction can be customized by the surgeon and that compression can be maintained while the surgeon executes a further process, such as a reduction of the fracture. Depending on the procedure, reducing the fracture often will move the portion of the bone on one side of the compression differently than the portion of the bone on the other side, and yet the cooperating, and movement accommodating relationship between cortical plate 1312 and malleable compression plate 210 enable the compression to be preserved, if desired, while this process occurs.

Additionally, the fit between cortical plate 1312 and compression plate 210 can be enhanced by reshaping a portion of outer surface 214 of compression plate 210 to include a flattened area as indicated by dashed line 246. The flattened surface portion 246 is shown as centered on a raised screw assembly 120, but it can also be disposed separately from screw assembly 120. It should also be understood that it is within the scope of the present disclosure for an embodiment to include a raised projection (not shown) extending outward from outer surface 214 that does not include a screw hole to be available for cooperative relationship with cortical plate 1312.

FIG. 14 illustrates a perspective view of a forked arm embodiment 1410 of malleable compression plate 210 (shown in FIG. 13) that includes arm 218 that forks at a predetermined region 1412 into a pair of separately malleable arm ends & prongs 1414 and 1416. Although arm 218 is shown in FIG. 14 as dividing into only two portions, arm 218 may divide into any number of portions at any location of forking region 1412.

Figures 15, 16:
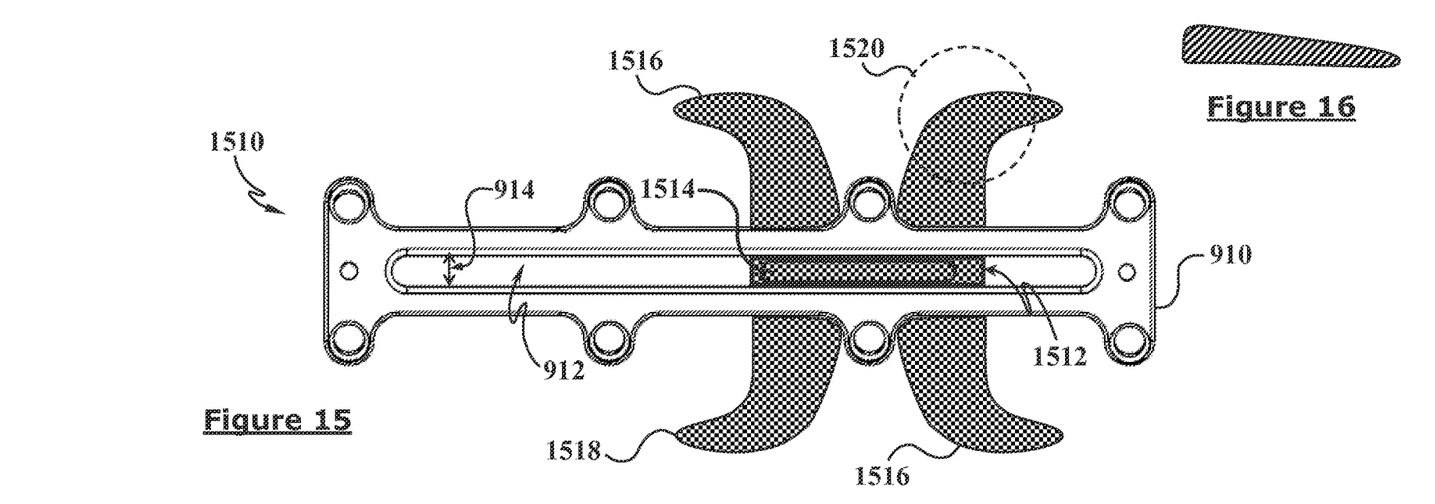
FIG. 15 is a top view of another embodiment of compression plate in a cooperative relationship with a representative cortical plate.
FIG. 16 is a cross-sectional view of a portion of compression plate 1512.

FIG. 15 is a top view of another embodiment of a malleable compression plate 1512 in a cooperative relationship with a representative cortical plate 910. FIG. 16 is a cross-sectional view of a portion of compression plate 1512. Compression plate 1512 includes an elongated projection 1514 sized to be received within elongated slot 912. Specifically, projection 1514 is both sized to fit unimpeded within a slot width 914, and shaped to enable only a single orientation direction, so that movement is limited to translation along the length of slot 912. Compression plate 1516 also includes multiple arms 1516 that provide additional degrees of freedom to vary the manner of construction of one malleable arm 1516 in use. Arms 1516 end in a terminal narrowing 1518, but do not include a prong per se, though one or more prongs can be included when needed.

Arm 1516 includes two shoulder regions 1520, shown in cross-section in FIG. 16. Shoulder region 1520 includes a normal direction that points toward the bone and a left side of cross-section is thicker than the right side to represent the outside of the curve of shoulder region 1520. As such, shoulder region 1520 includes a side to side thickness differential. A crimping of shoulder region 1520 will produce a 3-dimensional shape change, producing a cupping effect that can be controlled and made available for specific needs and situations.

Figure 17:
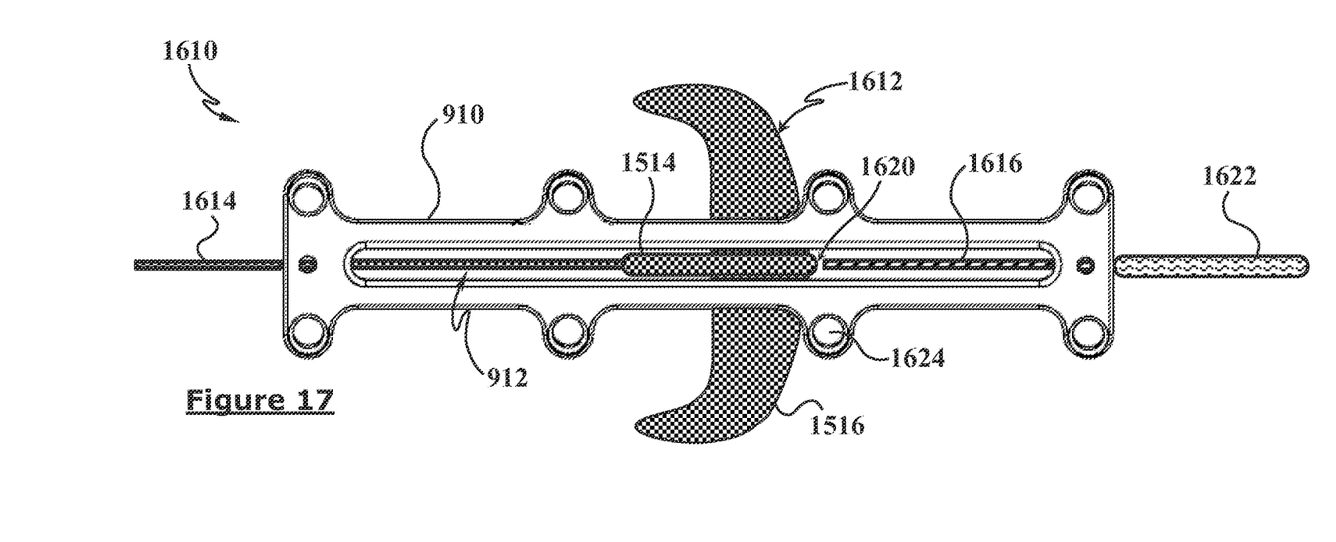
FIG. 17 is a top view of yet another embodiment of compression plate in a cooperative relationship with a representative cortical plate.

FIG. 17 is a top view of yet another embodiment of a malleable compression plate 1612 in a cooperative relationship with a representative cortical plate 910. As shown in FIG. 17, compression plate 1612 includes only a single arm 1516 as opposed to double arm compression plate 1512 shown in FIG. 15. Arm 1516 of compression plate 1612 is substantially similar to arms 1516 of compression plate 1512 (shown in FIG. 15). A wire 1614 is connected to projection 1514 and extends in line with elongated slot 912 from beneath plate 910 to provide a connection with, for example, and is affixed to another portion of the bone. A screw 1616 fits into a threaded aperture 1620 that enables a controlled force to pull projection 1514 to the right when a screw handle 1622 is turned since cortical plate 910 is anchored by at least one surgical screw affixed to the bone through at least one of screw holes 1624.

The compression thus produced does not require the surgeon to position and hold a clamp that can interfere with both the surgeon's vision as well as the available space for executing the orthopedic procedure. The compression force is applied to the fracture site such that compression of the fracture is maintained after the procedure is completed and the surgical site is closed. Differing degrees of relative freedom of movement between a specific embodiment of the malleable compression plate and a cooperating cortical plate are among the features of the present invention. These differing degrees of freedom include, but are not limited to, enabling up to 360 degrees of relative rotation, for example by ensuring that the raised screw assembly 120 is symmetrically round about the axis of the screw hole 122 (shown in FIG. 2), so that the plate 1312 can be spun about that axis without impedance. In other embodiments, it will be preferable to selectively constrain the relative motion of the cortical plate 1312 and malleable compression plate 210 (shown in FIG. 13).

Embodiments of the present disclosure are generally termed malleable compression plates, and are constructed of FDA approved surgically implantable metals, usually various alloys of stainless steel or titanium, though any suitable surgically implantable material is also utilizable, as long as it is malleable in a predictable manner.

The thicknesses of the compression plate can vary, in response to the requirements of the present utility, from approximately 0.1 millimeters (mm) up to approximately 3.0 mm. The variations in thickness can also follow gradients that are arranged relative to the longitudinal contours of the compression plate, so that when a compression force is applied, the response of the compression plate will vary, with the thinner portions being bent more than the thicker portions. As such, an application of an overall bending force across a region of varying thickness will produce a spatially varying bend that can selectively reconfigure the compression plate in three dimensions.

The compression plates described herein are at least partially malleable, such that at least one or more portions of the longitudinal extent of the malleable compression plate are designed to be selectively pliable. Malleability is defined herein as being amenable to reconfiguring with a force appropriate to surgical application, and includes reshaping and/or rearranging a resting arrangement so that when a bone portion prevents the reshaping to occur, the rearranged embodiment will exert forces on the bone preventing the reshaping. When an appropriate exertion of force is applied, the force reconfigures the malleable compression plate, so that the malleable compression plate will thereafter retain a memory of the new configuration, and continue to provide a compression and/or grip effect on the bone portion it is wrapped around.

The compression plates described herein include a bending feature that enables deflection of at least one portion of the compression plate to apply and/or maintain a compression force. One such bending feature is a plurality of score lines defined in the compression plate. A direction of a compression producing bend is definable with an appropriately scored plate portion which will bend along the score lines since they weaken the plate body along their length. Varying the placement and orientation of the score lines can also enable 3-dimensional reconfiguring of the compression plate to allow a surgeon to tailor a compression plate to a specific fracture site. An additional bending feature provides a bending segment having a thickness less than that of the adjacent plate portions such that the plate is malleable along a longitudinal length of the bending segment to allow for customization.

The compression plates described herein includes distal ends that include a terminal projection. The terminal projection may be shaped as a hook or an inwardly pointing triangular point. These ends can also be characterized, as prongs, hooks, pyramids, talons, and other well-known forms of narrowing shapes, depending on the utility needed. For example, an arm of the compression plate that ends in an inwardly pointing prong may also have hooked overall profile so that it can facilitate sliding movement of the malleable compression plate in one direction, but not another.

The malleable compression plate can also include varying assortments and arrangements of screw holes, k-wire holes, and raised projections, depending on the needs of the situation and the other equipment, most commonly cortical plates, with which the malleable compression plates will be used.

Also described herein is a compression plate assembly that includes a compression plate and a cortical plate. As described herein, the compression plate is coupled to the bone to apply and maintain compression on the fracture, and then the cortical plate is coupled on top of the compression plate. The cortical plate includes at least one elongated slot that receives a raised projection extending from the compression plate. The projection is sized appropriately to fit in the slot, and can be rounded to allow virtually unlimited relative rotational movement between the two plates even when the projection is nestled within the slot. Alternatively, the slot and/or the projection can be shaped to selectively limit the relative motion of the malleable compression plate and the cortical plate when the projection is in the slot. Additionally, the compression plate may include a flattened portion proximate the projections to provide an enhanced coupling of the two plates.

A number of other functionalities are also achievable with various embodiments of the present invention, including aiding in reducing and/or directing a fracture, when the application of the arms and/or a crimping of the arms when appropriately placed can help to achieve the reduction/distraction of a fracture. When a fracture has a spiral nature, the arms of the malleable compression plate can be configured to spiral in three dimensions to help to secure this type of fracture. If the fracture has a multitude of fragments needing to be held in a particular arrangement, the arms of the malleable compression plate, including more than one malleable compression plate working in coordination with each other, can provide significantly more flexible means of holding the fragments in place as desired until they are neutralized. Further manners of leveraging the relationship between the malleable compression plate and a cortical plate can include a screw driven malleable compression plate that has a projection cooperating with the direction constraints of a cortical plate's slot. If the slot is at least partially affixed to the bone, then using that plate as a leverage point to drive the malleable compression plate and/or its projection can effect a transmission of that force to another portion of bone through a translating wire attached to the malleable compression plate and/or its projection.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A compression plate for use with treating a fracture on a bone, said compression plate comprising:
    a curved and elongate main body portion comprising a central body portion and a pair of opposing end body portions, each of the opposing end body portions extending from the central body portion at a respective transition region, the main body portion having a bottom inner surface and a top outer surface, the top outer surface defining an outer arc and the bottom inner surface defining an inner arc, the inner arc having a radius greater than a radius of the outer arc such that the main body portion has a varying thickness, wherein said central body portion includes a first thickness and said pair of end body portions include a second thickness less than the first thickness, wherein the central body portion has a consistent first width and each opposing end body portion has a second width less than the first width, the width of the main body portion tapering from the first width to the second width within the transition region, and wherein a length of the main body portion between respective ends of said pair of opposing end body portions is greater than the first width of the central body portion, the length configured to be as transverse to a bone for which the compression plate is configured to be used with treating a fracture;

a pair of arms, each arm of said pair of arms extending from a respective end of said pair of opposing end body portions; and at least one score mark defined in said each arm such that said score mark defines a first arm portion and a second arm portion, wherein said first arm portion is moveable relative to said second arm portion about said at least one score mark such that said first arm portion and said second arm portion and the at least one score mark are configured to allow for deflection and application of a compression force on a bone when the compression plate is positioned around a bone, each arm configured to apply compression force on a bone by each said arm directly when the compression plate is positioned around a bone.

2. The compression plate in accordance with claim 1, wherein said at least one score mark comprises a plurality of score marks, each of the score marks of the plurality of score marks includes a respective orientation different than an orientation of every other score mark.

3. The compression plate in accordance with claim 1, wherein said each arm includes a distal end comprising at least one of a tapered point or a hooked prong.

4. The compression plate in accordance with claim 1, wherein said main body portion and said pair of arms form a C-shaped structure that defines a central void.

5. The compression plate in accordance with claim 1, wherein the main body portion further includes a screw assembly comprising:
an aperture configured to receive a screw; and
a shoulder extending upwardly and radially from the aperture.

6. A compression plate assembly for use with treating a fracture on a bone, said plate assembly comprising:
a compression plate comprising:
a curved and elongate main body portion comprising a central body portion and a pair of opposing ends, each of the opposing end body portions extending from the central body portion at a respective transition region, the main body portion having a bottom inner surface and a top outer surface, the top outer surface defining an outer arc and the bottom inner surface defining an inner arc, the inner arc having a radius greater than a radius of the outer arc such that the main body portion has a varying thickness, and wherein the central body portion has a consistent first width and each opposing end body portion has a second width less than the first width, the width of the main body portion tapering from the first width to the second width within the transition region;
a pair of arms, each arm of said pair of arms extending from a respective end of said pair of opposing ends; and
a bending segment positioned in each arm of said pair of arms and defining a first arm portion and a second arm portion, said first arm portion moveable relative to said second arm portion about said bending segment such that the bending segment is adapted and configured to avow for deflection and application of a compression force on a bone when the compression plate is positioned around the bone, each arm configured to apply the compression force on a bone directly when the compression plate is positioned around a bone, wherein said bending segment includes a first thickness and said first and second arm portions include a second thickness greater than the first thickness, wherein the first thickness of the bending segment is less than the second thickness of the first and second arm portions such that the second arm portion is adapted and configured to bend before the first arm portion when the compression plate is positioned around the bone;
wherein the first thickness is defined between an inner surface of said bending segment configured to be proximate the bone and an opposing outer surface of said bending segment, and wherein the second thickness is defined between an inner surface of said first and second arm portions configured to be proximate the bone and an opposing outer surface of said first and second arm portions; and
a cortical plate configured to be coupled to said compression plate such that the compression plate is positioned between the bone and said cortical plate, the cortical plate comprising an upper surface and a lower surface, the upper surface and the lower surface being curved and parallel such that the cortical plate is rounded in profile, the lower surface is configured to interface with the top outer surface of the compression plate, the length configured to be defined as transverse to a bone for which the compression plate is configured to be used with treating a fracture.

7. The compression plate assembly in accordance with claim 6, wherein said compression plate includes the one or more arms configured to interface with said cortical plate.

8. The compression plate assembly in accordance with claim 6, wherein said cortical plate includes at least one elongated slot.

9. The compression plate assembly in accordance with claim 8, wherein said compression plate includes at least one screw assembly comprising a shoulder projection and a screw aperture.

10. The compression plate assembly in accordance with claim 9, wherein said slot is sized and configured to receive said shoulder projection therein such that said cortical plate is movable along said slot.

11. The compression plate assembly in accordance with claim 9, wherein said shoulder projection includes a substantially rounded profile such that said cortical plate is configured to be rotatable about said shoulder projection.

12. The compression plate assembly in accordance with claim 6, wherein the main body portion further includes a screw assembly comprising:
an aperture configured to receive a screw; and
a shoulder extending upwardly and radially from the aperture.

13. The compression plate assembly in accordance with claim 12 further comprising a cortical plate, the cortical plate comprising at least one elongated slot configured to receive the shoulder of the screw assembly.

14. The compression plate assembly in accordance with claim 13, wherein the cortical plate further comprises at least one screw hole separate from the at least one elongated slot.

* * * * *

UNITED STATES PATENT AND TRADEMARK OFFICE
CERTIFICATE OF CORRECTION

PATENT NO. : 10,835,301 B1  
APPLICATION NO. : 14/657718  
DATED : November 17, 2020  
INVENTOR(S) : Amod P. Paranjpe, A. Jamie Riley and Gary J. Schmidt Page 1 of 1

It is certified that error appears in the above-identified patent and that said Letters Patent is hereby corrected as shown below:

In the Claims

Claim 1 - Column 9, Line 11 - should read "...to be defined as transverse to a bone..."

Claim 6 - Column 10, Line 3 - "avow for deflection" should read "allow for deflection."

Signed and Sealed this  
Twenty-fifth Day of May, 2021

Drew Hirshfeld  
*Performing the Functions and Duties of the*  
*Under Secretary of Commerce for Intellectual Property and*  
*Director of the United States Patent and Trademark Office*